United States Patent
Canning et al.

(10) Patent No.: US 10,930,390 B2
(45) Date of Patent: Feb. 23, 2021

(54) TASK MANAGEMENT TOOL FOR PATIENT DISCHARGE

(71) Applicant: INTERNATIONAL BUSINESS MACHINES CORPORATION, Armonk, NY (US)

(72) Inventors: Caroline R. Canning, Chicago, IL (US); Gina M. Cardosi, Chicago, IL (US); Paul C. Castro, Sharon, MA (US); Lucy L. Chen, Lancaster, PA (US); Patrick M. Clough, Bloomington, IL (US); Matt Harper, Chicago, IL (US); John J. Mutter, Mt. Pleasant, SC (US); Ji Young Roe, Northbrook, IL (US)

(73) Assignee: International Business Machines Corporation, Armonk, NY (US)

( * ) Notice: Subject to any disclaimer, the term of this patent is extended or adjusted under 35 U.S.C. 154(b) by 950 days.

(21) Appl. No.: 15/064,753

(22) Filed: Mar. 9, 2016

(65) Prior Publication Data
US 2017/0262591 A1  Sep. 14, 2017

(51) Int. Cl.
*G16H 40/20* (2018.01)
*G06Q 10/06* (2012.01)

(52) U.S. Cl.
CPC ....... *G16H 40/20* (2018.01); *G06Q 10/06311* (2013.01); *G06Q 10/063114* (2013.01)

(58) Field of Classification Search
CPC ...................................................... G16H 40/20
See application file for complete search history.

(56) References Cited

U.S. PATENT DOCUMENTS

| | | | |
|---|---|---|---|
| 2007/0142713 A1* | 6/2007 | Lancaster | G06Q 50/22 600/300 |
| 2007/0143143 A1 | 6/2007 | Villasenor et al. | |
| 2008/0164998 A1 | 7/2008 | Scherpbier et al. | |
| 2010/0305966 A1 | 12/2010 | Coulter et al. | |
| 2011/0071851 A1* | 3/2011 | Alden | G06Q 10/06 705/3 |
| 2013/0073344 A1 | 3/2013 | Parent | |
| 2014/0108035 A1 | 4/2014 | Akbay et al. | |
| 2015/0066529 A1 | 3/2015 | Lattuca et al. | |
| 2015/0134363 A1 | 5/2015 | Gibson | |
| 2016/0117458 A1* | 4/2016 | Hermans | G16H 40/63 705/2 |
| 2018/0226141 A1* | 8/2018 | Slepian | G06F 19/00 |

* cited by examiner

*Primary Examiner* — Rachelle L Reichert
(74) *Attorney, Agent, or Firm* — Brian D. Welle

(57) ABSTRACT

A hospital discharge performance system and computer-implemented method for integrating and recording both planned clinical activity and non-clinical barriers to patient discharge. One or more non-clinical barriers are received from at least one remote input device configured to record barriers in close proximity to the occurrence of the barrier and stored in the a non-clinical barrier database. Clinical tasks that need to be performed prior to discharge are integrated with non-clinical barriers that must be overcome to provide an indication of at least one patient's current status with respect to discharge. Update information indicating progress toward completion of planned clinical activity and progress toward overcoming the received one or more non-clinical barriers is received from at least one remote input device. The occurrences of barriers are summarized across a selected group of patient discharges and a report is generated.

19 Claims, 4 Drawing Sheets

TASK MANAGEMENT TOOL FOR PATIENT DISCHARGE

BACKGROUND

This disclosure relates to task management systems, and more specifically, to a task management tool to optimize the performance of patient discharge tasks at healthcare facilities.

Bed management is a common problem in healthcare facilities, such as hospitals and skilled nursing facilities. Patients, who are ready to be discharged from a hospital or other healthcare facility, may occupy a bed (and all its associated resources) for hours due to the ad hoc nature in which discharge tasks are performed. Other patients may be awaiting beds in other departments of the healthcare facility until the discharge tasks are completed. The unnecessary wait time for these tasks can be hours or, in some cases, days. Optimizing the performance of discharge tasks will benefit the entire flow of patients from admittance, to movement within departments, and finally being discharged (removed from care) from the healthcare facility.

One of the difficulties in task management for healthcare facilities is the dynamic nature of the status of patients while performing both clinical and non-clinical tasks. Unlike processes that adhere to strict workflows (e.g., manufacturing), patient care is a complex, dynamic process that requires knowledge-intensive activities and is subject to numerous unforeseen circumstances that can prevent or delay completion of required tasks, as well as other tasks that are dependent upon the completion of earlier task(s).

Once a patient has been approved for discharge, any unplanned task/event that is a barrier to discharge ("barrier") becomes an important metric that needs to be monitored and managed. Current task management systems are not optimized for the complex, dynamic nature of a hospital environment that includes both clinical and non-clinical tasks, and most medical facility IT systems are not designed to capture dynamic, ad hoc data, but instead focus on electronic storage and retrieval of patient records.

SUMMARY

In one aspect of this disclosure, a hospital discharge performance system and computer-implemented method are disclosed for integrating and recording both planned clinical activity and non-clinical barriers to patient discharge. The system includes at least one clinical task management database, at least one non-clinical barriers database, at least one processor, and non-transient memory that stores program instructions which, when executed by the at least one processor, cause the at least one processor to receive one or more non-clinical barriers from at least one remote input device configured to record barriers in close proximity to the occurrence of the barrier and store the received non-clinical barriers in the at least one non-clinical barrier database. Clinical tasks that need to be performed prior to discharge are integrated with non-clinical barriers that must be overcome in order to provide an indication of at least one patient's current status with respect to discharge. Update information indicating progress toward completion of planned clinical activity is received from at least one input device. Update information indicating progress toward overcoming the received one or more non-clinical barriers is received from at least one remote input device. The occurrences of barriers are summarized across a selected group of patient discharges and a report is generated.

In another aspect of this disclosure, a computer-implemented method is disclosed for integrating and recording both planned clinical activity and non-clinical barriers to patient discharge. The following are performed for at least two patients using a first computer program product: (a) retrieving clinical tasks from at least one clinical task database, (b) receiving a status update about one or more non-clinical barriers, (c) integrating the clinical tasks with the one or more non-clinical barriers and displaying the current discharge status for a patient, and (d) determining whether the patient has been discharged. The non-clinical barriers are summarized from a group selected from the at least two patients and a report is generated using a second computer program product.

According to another embodiment of the present invention, a method of integrating and recording both planned clinical activity and non-clinical barriers to patient discharge using a one or more computer program product comprising for at least two patients and summarizing the data related to the barriers from a group selected group of patients and producing a report.

DETAILED DESCRIPTION

This disclosure provides a technical solution to optimize the discharge of patients from a healthcare facility, while, at the same time, collecting data related to barriers to patient discharge for individual patients and analyzing and summarizing that data across selected patient groups.

Figure 1:
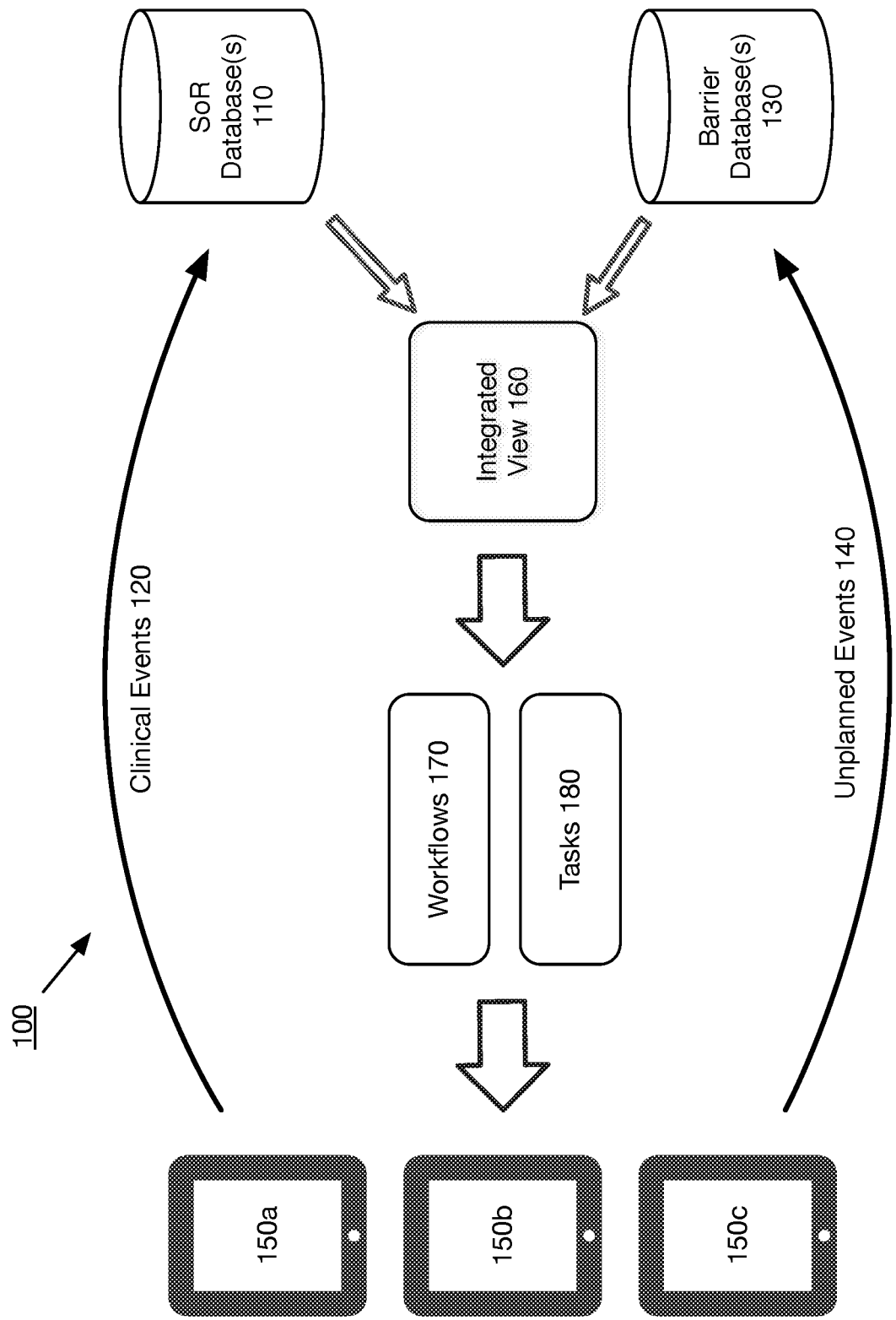
FIG. 1 shows, in simplified form, a high level abstract diagram of an illustrative network capable of implementing the task management tool.

FIG. 1 shows, in simplified form, a high level abstract diagram of an illustrative network 100 capable of implementing an embodiment of the task management tool described herein. The illustrative network 100 includes one of more clinical task management databases 110, which record clinical events 120 associated with the treatment of patients. The clinical task management database(s) 110 may be a component of a single system or accessible information located in a separate database, such as (but not limited to) a System of Record (SoR) or electronic medical record (EMR) database.

The illustrative network 100 includes one or more non-clinical barriers databases 130 configured to record barriers or unplanned events 140 associated with the discharge of a patient. Examples of non-clinical barriers include (but are not limited to) the patient is asleep or not in the room so that a task cannot be completed, an equipment issue has prevented completion of a task, the patient has declined consent to complete a task required prior to discharge, etc. The non-clinical barriers database(s) 130 may be part of a single system or accessible information located in a separate database.

One or more remote input computing devices 150a, 150b, 150c can be used by healthcare professionals to record progress towards completion of planned clinical events 120, which information is stored in the clinical task management database(s) 110. The remote computing devices 150a, 150b, 150c can also be used by healthcare professionals to record and display progress towards overcoming barrier(s) 140, which information is stored in barrier database(s) 130. Remote computing devices 150a, 150b, 150c may be, for example, a smart phone (e.g., an iPhone® or Android® handheld device), tablet computer (e.g. an iPad® or Windows® Surface® tablet computer), personal digital assistant (PDA), laptop computer, or any other computing device capable of accepting user input and transmitting/receiving data over a wireless network.

As shown in FIG. 1, the task management tool provides an integrated view 160 of workflows 170 and tasks 180 that can be displayed on the remote computing devices 150a, 150b, 150c to provide an accurate indication of the status of tasks required to be completed prior to discharge of a patient, as well as barriers preventing the completion of those tasks.

While three remote computing devices 150a, 150b, 150c are shown in the illustrative network 100, it is understood that the task management tool may be implemented using any number of remote computing devices and is not limited to the three devices shown in FIG. 1. The first computing device 150a in the illustrative example in FIG. 1 may, for instance, include application software (210a in FIG. 2) executable by a processing unit that a staff nurse may utilize to record clinical events 120 and unplanned barrier events 140 in connection with the discharge of a particular patient.

The second computing device 150b may, for example, include application software (210b in FIG. 2) executable by a processing unit that a charge nurse may utilize to give a comprehensive view of all patients in an entire ward or department. The application software also allows the charge nurse to drill down into individual rooms and patients to view workflows, tasks to be completed before a particular patient may be discharged. The second computing device 150b may also be configured to record clinical events 120 and unplanned barrier events 140 in connection with the discharge of a particular patient.

The third computing device 150c may, for example, include application software (210c in FIG. 2) executable by a processing unit that a doctor may utilize to view, for instance, what patients have been checked in since the doctor's shift began, which patients are scheduled to be discharged that day, overall what patients the doctor is in charge of, etc. The third computing device 150c may also be used to view workflows and tasks to be completed before the patient can be discharged. The third computing device 150c may also be configured to record clinical events 120 and unplanned barrier events 140 in connection with the discharge of a particular patient.

Figure 2:
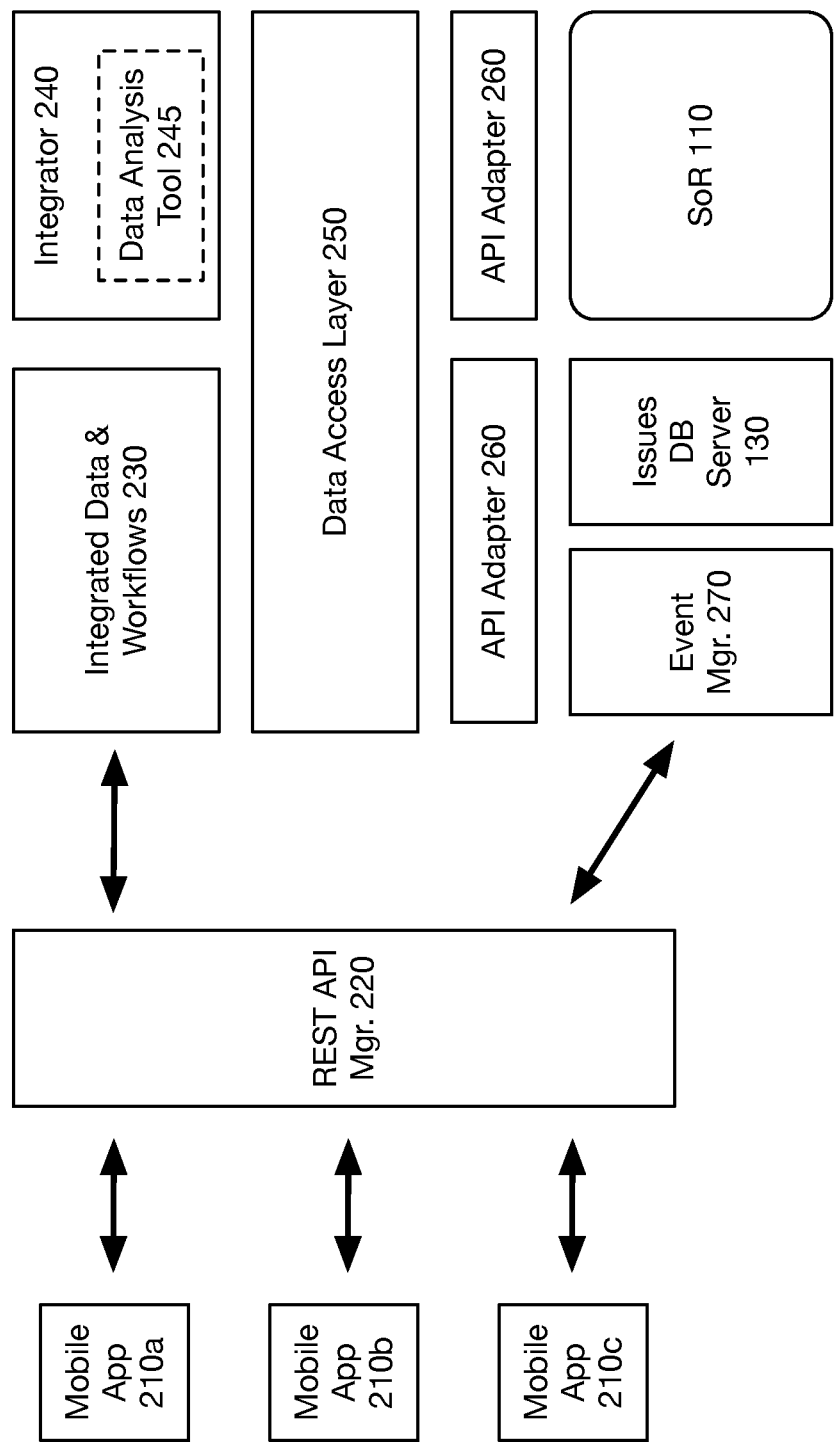
FIG. 2 shows, in simplified form, representative components of the task management tool of FIG. 1.

FIG. 2 shows, in simplified form, representative components of the task management tool. Mobile application (app) software 210a, 210b, 210c are client-side applications running on remote computing devices 150a, 150b, 150c, respectively. Mobile app 210a, 210b, 210c each implement a user interface and workflow logic for supporting patient discharge activities.

However, in order for the needed data to be expeditiously recorded, it is advantageous that the input devices 130 configured to record barriers be in close proximity to the occurrence of the barrier and ideally is a mobile device. The term "close proximity" should be understood to encompass one or both of either physical distance (e.g., same room, same floor, . . . etc.) and/or time (during patient care activities, just after patient care activities, within a few minutes of completion of patient care, within 30 minutes of completion of patient care, . . . etc.).

The information in both database 110, 120 is accessed by the task integrator 140 (a computer program product), which is configured to integrate this information as well as updates from the one or more input devices 150, 160 for recording progress in order to provide an indication of the patient's current status with respect to discharge.

A REST API manager 220 preferably implements a network protocol interface to various cloud components implementing the task management tool described herein.

Integrated Data and Workflows 230 is a store for integrated representations of the data and workflows.

Integrator 240 is server-side logic configured to encode how clinical and non-clinical data should be combined.

Data Access Layer 250 is configured to implement interface for Integrator 240 to manage data used in its logic.

API Adaptor 260 is configured to present a "normalized" interface to the Data Access Layer 250 that allows actual calls to underlying storage systems.

Event Manager 270 is an optional component that can be called by the REST API manager 220 whenever a client makes an API call to register important events, such as "new data entered," "data deleted," etc. This can trigger Integrator 240 to recalculate the integrated view.

Issues DB Server (Barrier Database) 130 is a database capable of storing semi-structured information about unplanned, non-clinical events.

In one embodiment, Systems of Record (SoR) 110 may be a SoR database, which may already be used by the healthcare facility and cannot be modified.

It should be noted that there are several ways in which the integration can be accomplished and a few representative examples will now be discussed.

In one embodiment, the task integrator 240 uses user input supplied by the users to integrate and prioritize the clinical tasks and barriers to be completed. In another embodiment, barriers are assumed to be more immediate than the current clinical task to be completed. In still another embodiment, the task integrator 240 is an expert system that uses its knowledge-base to determine the priority based on one or more of a set of rules and/or calculated impact on discharge time. In further embodiments, the task integrator 240 is a combination of the previously mentioned embodiments. The point being, not the particular method of integration that occurs, but simply that task integration occurs in a manner sufficient to provide an indication of the patient's current discharge status.

Aside from prioritizing the tasks and barriers, it is advantageous to incorporate as part of the task integrator 240 the ability to assign clinical tasks and barriers to either individuals or roles. For example, a primary nurse may need to take vitals of a patient prior to discharge. If upon arrival in the patient's room, the primary nurse discovers that the patient is no longer in the patient's room and has been taken for testing on another floor, the primary nurse can record the non-clinical barrier within the barriers database 130 that she was unable to take vitals due to the patient not being in the room.

A few exemplary embodiments of how roles can be assigned will now be presented.

In one embodiment, this barrier could either remain the responsibility of this same primary nurse until completed. In another embodiment, the primary nurse or the supervisory "charge" nurse that oversees the primary nurse has the ability to assign this non-clinical task to either another individual or to a particular role, such as (but not limited to)

certified health care provider or nurse. The assignment to a role can be particularly advantageous because, in this example, the certified health care provider currently performing the testing may be able to resolve this non-clinical barrier. In still other embodiments, the assignment is done via an expert system that uses a knowledge base of both barriers and staff availability to assign barriers to particular staff members or roles. In further embodiments, the assignment is performed through a combination of the previously mentioned embodiments. The point being not the particular method of assignment used, but simply that assignment of tasks is advantageous in facilitating discharge, regardless of the form it takes.

The Integrator 240 preferably includes one or more data analysis tools 245 configured to summarize the occurrences of barriers across a selected group of patient discharges and produce reports. The data analysis tool(s) 245 is configured to accept data from at least one or more of: the one or more non-clinical barriers databases 130, the one of more clinical task management databases 110, and/or the task integrator 240 (if the data analysis tool 245 is a separate component from Integrator 240). The reports produced by the data analysis tool(s) 245 can range from simple frequency of occurrence of particular barriers to complex time studies of the impact of barriers on the length of discharge. It should be noted that the data analysis tool(s) 245 may be separate from or a component of the task integrator 240.

In usage, barriers are any activity that has a potential negative impact on the current planned discharge that is not currently a clinical task. Barriers may either be non-clinical tasks, such as (but not limited to) packing up all the patient's personal belongings, or may be clinical activities (e.g., taking a patient's vitals) that were not specified as a retrievable clinical task but still need to be performed prior to discharge. A staff member (e.g., a primary nurse) can enter barriers using remote computing device 150, which have an associated task to be completed. These barriers may include (but are not limited to) patient requests, issues, and other unplanned events that change the nature or prevent a task from being completed (e.g., the patient is not in the room, the printer is out of ink, etc.). The task management tool allows the entry of these barriers to be received by the task integrator 240 and integrated with more traditional clinical tasks. Using this additional data, nurses, doctors and other staff have better access to the real-time status of all discharge activities and can more easily assign appropriate resources to improve the time for patient discharge and bed wait times.

In one embodiment, data entry of the barriers using the one or more remote computing devices 150 is performed as a semi-structured data item that includes a creation time, due date or time, and free text entry of what task is associated with the barrier that needs to be completed. This last item can also be entered from a pre-existing selection (drop down) list or menu that contains text for more common tasks associated with a barrier, such as (but not limited to) "check vital signs," "patient not in room," "equipment malfunction," "patient refused," etc. Once the barrier task is entered and subsequently integrated by the task integrator 240, the barrier can be monitored on a computer, mobile device, or wearable computing device.

Having described an example system, an illustrative method of implementing the technical solution using a computer program product will now be described.

Figure 3:
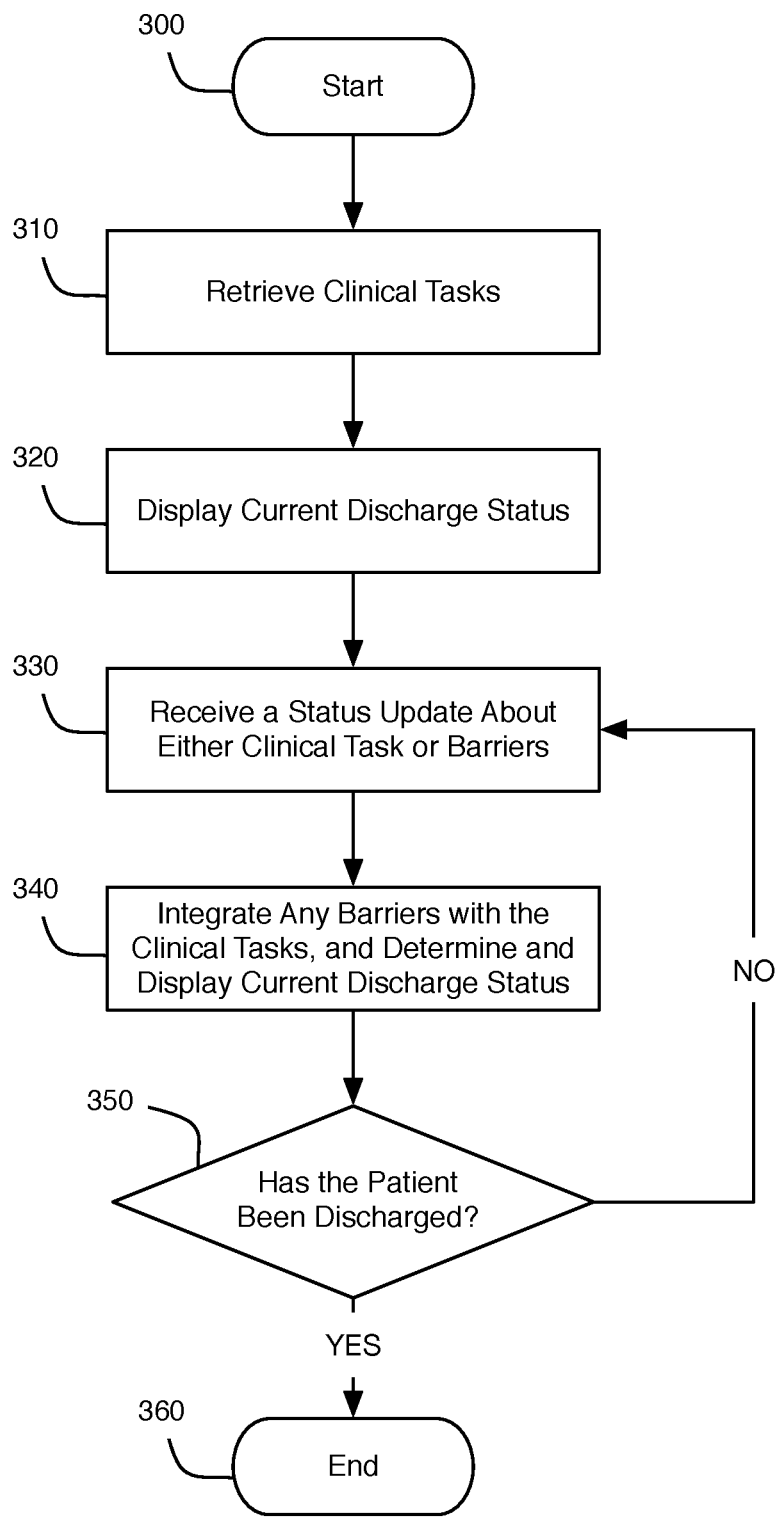
FIG. 3 shows, in simplified form, a representative individual patient process capable of implementing the initial portion of the technical solution described herein.

FIG. 3 shows, in simplified form, a representative individual patient process 300 capable of implementing the initial portion of the technical solution described herein. Once the individual process 300 has been performed on more than one patient, in order to complete the technical solution, the data related to the barriers (and clinical tasks) can be analyzed, summarized and reported across a selected group of patients.

Referring to FIG. 3, the clinical tasks are retrieved (Step 310) and the current discharge status is displayed (Step 320). The current discharge status will remain unchanged until either an update is received regarding a clinical task to be performed or barrier is either entered or updated (Step 330).

Once an update is received (Step 330), any barriers are integrated with the clinical tasks to determine the patient's current discharge status (Step 340).

A determination is made, based upon the updated status, if the patient has been discharged. If so, then the individual patient process 300 ends (Step 360). If not, then the process 300 returns to waiting to receive a status update (Step 330).

Figure 4:
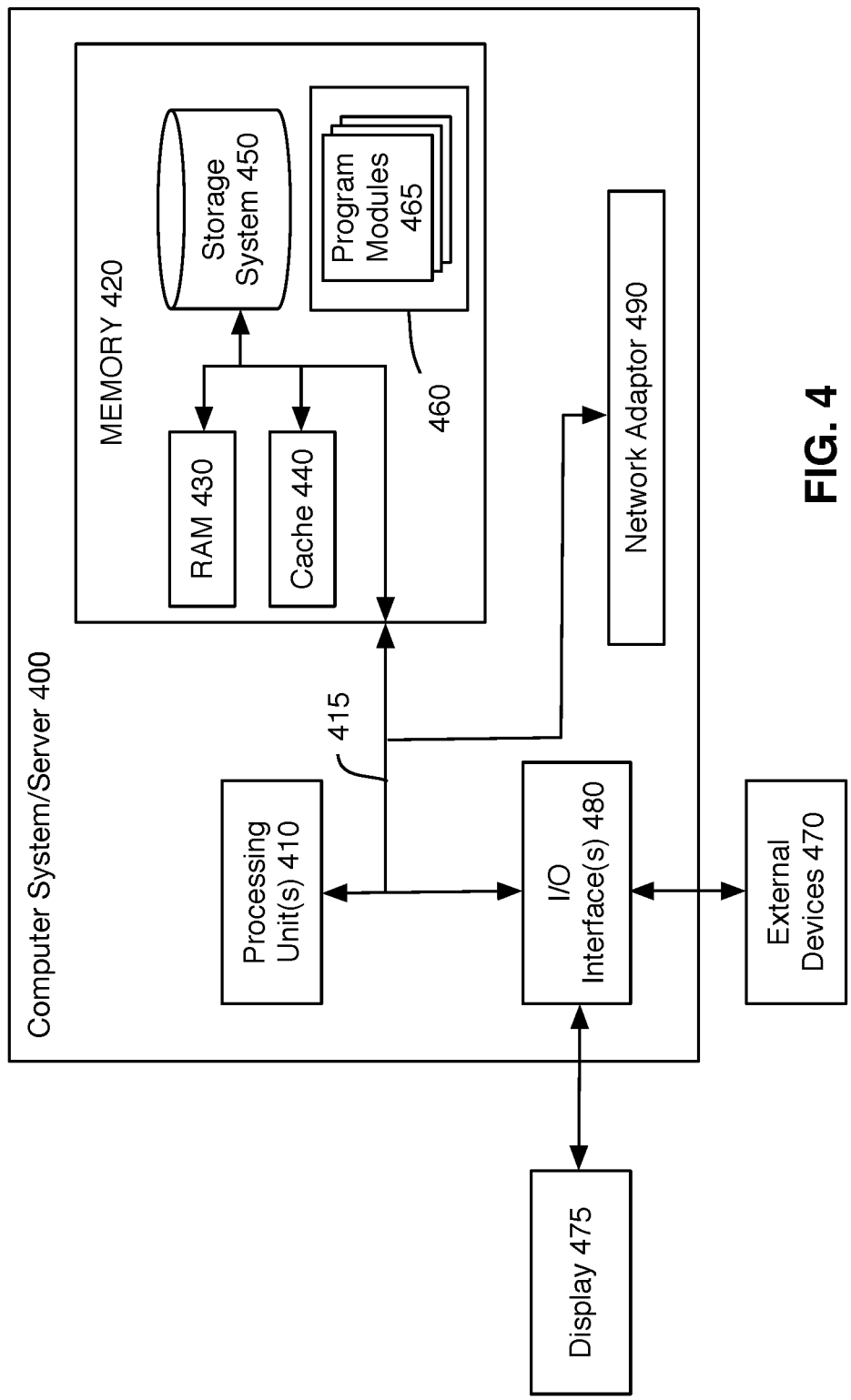
FIG. 4 is a block diagram of an illustrative server/computing device that may be utilized to implement the various features and processes described herein.

Referring to FIG. 4, a block diagram of an illustrative computer system/server 400 is shown that may be utilized to implement the various features and processes described herein. Computer system/server 400 is only one example of a suitable server or computer system and is not intended to suggest any limitation as to the scope of use or functionality of embodiments of the invention described herein. Regardless, computer system/server 400 is capable of being implemented and/or performing any of the functionality set forth hereinabove.

Server/computing device 400 is operational with numerous other general purpose or special purpose computing system environments or configurations. Examples of well-known computing systems, environments, and/or configurations that may be suitable for use with computer system/server 400 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

[Computer system/server 400 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 400 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 400 is shown in the form of a general-purpose computing device. The components of computer system/server 400 may include, but are not limited to, one or more processors or processing units 410, a system memory 420, and a bus 415 that couples various system components including system memory 420 to processing unit(s) 410.

Bus 415 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 400 typically includes a variety of computer system readable media. Such media may be any available media that is accessible by computer system/server 400, and it includes both volatile and non-volatile media, removable and non-removable media.

System memory 420 can include computer system readable media in the form of volatile memory, such as random access memory (RAM) 430 and/or cache memory 440. Computer system/server 400 may further include other removable/non-removable, volatile/non-volatile computer system storage media. By way of example only, storage system 450 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 415 by one or more data media interfaces. As will be further depicted and described below, memory 420 may include at least one program product having a set (e.g., at least one) of program modules that are configured to carry out the functions of embodiments of the invention.

Program/utility 460, having a set (at least one) of program modules 465, may be stored in memory 420 by way of example, and not limitation, as well as an operating system, one or more application programs, other program modules, and program data. Each of the operating system, one or more application programs, other program modules, and program data or some combination thereof, may include an implementation of a networking environment. Program modules 465 generally carry out the functions and/or methodologies of embodiments of the invention as described herein.

Computer system/server 400 may also communicate with one or more external devices 470 such as a keyboard, a pointing device, a display 475, etc.; one or more devices that enable a user to interact with computer system/server 400; and/or any devices (e.g., network card, modem, etc.) that enable computer system/server 400 to communicate with one or more other computing devices. Such communication can occur via Input/Output (I/O) interfaces 480. Still yet, computer system/server 400 can communicate with one or more networks such as a local area network (LAN), a general wide area network (WAN), and/or a public network (e.g., the Internet) via network adapter 490. As depicted, network adapter 490 communicates with the other components of computer system/server 400 via bus 415. It should be understood that although not shown, other hardware and/or software components could be used in conjunction with computer system/server 400. Examples, include, but are not limited to: microcode, device drivers, redundant processing units, external disk drive arrays, RAID systems, tape drives, and data archival storage systems, etc.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN)

or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A hospital discharge performance system for integrating and recording both planned clinical activity and non-clinical barriers to patient discharge, comprising:
    clinical task management database;
    non-clinical barriers database;
    at least one processor;
    non-transient memory that stores program instructions which, when executed by the at least one processor, cause the at least one processor to: provide a representational state transfer (REST) application programming interface (API) to receive requests from and generate responses to a plurality of remote mobile computing devices, each remote mobile computing device executing a mobile app;
    receive, via the REST API and from the mobile app being executed by a first remote mobile computing device of the plurality of remote mobile computing devices, one or more non-clinical barriers recorded in close proximity to an occurrence of each barrier;
    receive, via the REST API and from the mobile app being executed by the first remote mobile computing device, one or more clinical tasks that have been performed or are not yet performed;
    receive, via the REST API and from the mobile app being executed by one of the plurality of remote mobile computing devices, real-time update information indicating an unplanned non-clinical barrier from one of the plurality of remote mobile computing devices;
    integrate, via the REST API, the unplanned non-clinical barrier into the non-clinical barriers in the non-clinical barriers database;
    store the received non-clinical barriers in the non-clinical barriers database;
    store the received clinical tasks in the clinical task management database;
    integrate both clinical tasks that need to be performed prior to discharge with non-clinical barriers that must be overcome in order to provide an indication of at least one patient's current status with respect to discharge;
    receive real-time update information indicating progress toward completion of planned clinical activity from one of the plurality of remote mobile computing devices; receive real-time update information indicating progress toward overcoming the received one or more non-clinical barriers from one of the plurality of remote mobile computing devices; and
    summarize the occurrences of barriers across a selected group of patient discharges and generate a report for display on one of the plurality of remote mobile computing devices other than the first remote mobile computing device such that the report reflects real-time data on progress of the selected group of patients regarding both the planned clinical activity and the non-clinical barriers.

2. The system of claim 1, wherein the program instructions are further configured to cause the at least one processor to perform assignment of non-clinical barriers.

3. The system of claim 2, wherein the plurality of remote mobile devices comprises a second remote mobile computing device associated with a second individual other than a first individual operating the first remote mobile computing device, and wherein the assignment of non-clinical barriers is to the second individual and wherein an assigned non-clinical barrier is displayed on the second remote mobile computing device.

4. The system of claim 2, wherein the plurality of remote mobile devices comprises a second remote mobile computing device associated with a second individual having a second role other than a first role of a first individual operating the first remote mobile computing device, wherein the assignment of non-clinical barriers is to the second role, and wherein an assigned non-clinical barrier is displayed on the second remote mobile computing device based at least in part on the second individual being a member of the second role.

5. The system of claim 1, wherein each non-clinical barrier received from the at least one remote mobile computing device includes at least a creation time, due date, and task associated with the received non-clinical barrier.

6. The system of claim 5, wherein the task associated with the received non-clinical barrier is selected from a pre-existing selection list displayed on the first remote mobile computing device.

7. The system of claim 1, wherein close proximity relates to physical distance.

8. The system of claim 1, wherein close proximity relates to time.

9. A computer implemented method of integrating and recording both planned clinical activity and non-clinical barriers to patient discharge, comprising:
performing the following for at least two patients using a first computer program product:
retrieving clinical tasks from at least one clinical task database;
receiving, via a representational state transfer (REST) application programming interface (API) provided by the first computer program product, a real-time status update about one or more non-clinical barriers from a first remote mobile computing device;
receiving, via the REST API and from a mobile app being executed by one of a plurality of remote mobile computing devices, real-time update information indicating an unplanned non-clinical barrier from one of the plurality of remote mobile computing devices;
integrating, via the REST API, the unplanned non-clinical barrier into the non-clinical barriers in the non-clinical barriers database;
integrating the clinical tasks with the one or more non-clinical barriers and displaying a current discharge status for a patient; and
determining whether the patient has been discharged; and
summarizing an occurrence of the one or more the non-clinical barriers from a group selected from the at least two patients, generating a report using a second computer program product, and causing display of the report on a remote mobile computing device other than the first remote mobile computing device, such that the report reflects real-time data on progress of the selected group of patients regarding both the planned clinical activity and the non-clinical barriers.

10. The computer implemented method of claim 9, wherein the receiving further includes a status update about one or more clinical tasks.

11. The computer implemented method of claim 9, wherein the integrating also includes an assignment of barriers.

12. The computer implemented method of claim 11, wherein a second remote mobile computing device is associated with a second individual having a second role other than a first role of a first individual operating the first remote mobile computing device, wherein the assignment is to the second role, and wherein an assigned non-clinical barrier is displayed on the second remote mobile computing device based at least in part on the second individual being a member of the second role.

13. The computer implemented method of claim 11, wherein the first and second computer program products are components of a larger computer program product.

14. A computer-implemented method for integrating and recording both planned clinical activity and non-clinical barriers to patient discharge, comprising:
receiving, using a representational state transfer (REST) application programming interface (API) being provided by at least one processor and from a first remote mobile computing device of a plurality of remote mobile computing devices, one or more non-clinical barriers recorded in close proximity to an occurrence of each barrier;
receiving, using the REST API and from the first remote mobile computing device, clinical tasks that have been performed or have yet to be performed;
receive, via the REST API and from a mobile app being executed by one of the plurality of remote mobile computing devices, real-time update information indicating an unplanned non-clinical barrier from one of the plurality of remote mobile computing devices;
integrate, via the REST API, the unplanned non-clinical barrier into the non-clinical barriers in a non-clinical barriers database;
storing, using the at least one processor, the received non-clinical barriers in at least one non-clinical barriers database;
storing, using the at least one processor, the received clinical tasks in at least one clinical task management database;
integrating, using the at least one processor, both clinical tasks that need to be performed prior to discharge with non-clinical barriers that must be overcome in order to provide an indication of at least one patient's current status with respect to discharge;
receiving, using the REST API, real-time update information indicating progress toward completion of planned clinical activity from at least one of the plurality of the remote mobile computing devices;
receiving, using the REST API, real-time update information indicating progress toward overcoming the received one or more non-clinical barriers from at least one of the plurality of the remote mobile computing devices; and
summarizing the occurrences of barriers across a selected group of patient discharges and generating a report for display on a remote mobile computing device different from the first remote mobile computing device, such that the report reflects real-time data on progress of the selected group of patients regarding both the planned clinical activity and the non-clinical barriers.

15. The computer-implemented method of claim 14, a second remote mobile computing device is associated with a second individual having a second role other than a first role of a first individual operating the first remote mobile computing device, and further comprising assigning, using at least one processor, non-clinical barriers to at least one of the second individual or the second role, and wherein an assigned non-clinical barrier is displayed on the second remote mobile computing device based at least in part on the second individual's identity or membership in the second role.

16. The computer-implemented method of claim 14, wherein each non-clinical barrier received from the first remote mobile computing device includes at least a creation time, due date, and task associated with the received non-clinical barrier.

17. The computer-implemented method of claim 16, wherein the task associated with the received non-clinical barrier is selected from a pre-existing selection list displayed on the first remote mobile computing device.

18. The computer-implemented method of claim 14, wherein close proximity relates to physical distance.

19. The computer-implemented method of claim 14, wherein close proximity relates to time.

\* \* \* \* \*